United States Patent
Brandt et al.

(10) Patent No.: US 11,384,202 B2
(45) Date of Patent: Jul. 12, 2022

(54) WATER-SOLUBLE POLYAMIDE POLYMER AND USE THEREOF AS FUNCTIONAL ADDITIVE

(71) Applicant: Henkel AG & Co. KGaA, Duesseldorf (DE)

(72) Inventors: Adrian Brandt, Essen (DE); Horst Beck, Neuss (DE); Luca Mario Marchese, Arese (IT); Sebastiano Moscardin, Dorno (IT); Alexander Schulz, Essen (DE); Michael Strotz, Cologne (DE); Lisa Mareike Noack, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/752,068

(22) Filed: Jan. 24, 2020

(65) Prior Publication Data

US 2020/0157281 A1    May 21, 2020

Related U.S. Application Data

(63) Continuation of application No. PCT/EP2018/069961, filed on Jul. 24, 2018.

(30) Foreign Application Priority Data

Jul. 25, 2017  (EP) .................................... 17182956

(51) Int. Cl.
| | |
|---|---|
| *C08G 69/28* | (2006.01) |
| *C08G 69/40* | (2006.01) |
| *C08L 77/00* | (2006.01) |
| *C08L 77/06* | (2006.01) |

(52) U.S. Cl.
CPC ............. *C08G 69/28* (2013.01); *C08G 69/40* (2013.01); *C08L 77/00* (2013.01); *C08L 77/06* (2013.01)

(58) Field of Classification Search
CPC ......... C08L 77/00; C08L 77/06; C08G 69/26; C08G 69/40
See application file for complete search history.

(56) References Cited

U.S. PATENT DOCUMENTS

| | | | |
|---|---|---|---|
| 4,420,608 A | 12/1983 | Morello | |
| 4,619,775 A | 10/1986 | Steltenkamp et al. | |
| 5,804,313 A * | 9/1998 | Schell | C03C 25/26 428/373 |
| 2008/0145696 A1* | 6/2008 | Senkfor | C08G 18/12 428/423.1 |
| 2017/0044320 A1* | 2/2017 | Duan | C08K 3/00 |
| 2017/0340553 A1 | 11/2017 | Anderheggen et al. | |
| 2018/0008524 A1 | 1/2018 | Anderheggen et al. | |

FOREIGN PATENT DOCUMENTS

| | | |
|---|---|---|
| WO | 9608538 A1 | 3/1996 |
| WO | 9822478 A1 | 5/1998 |
| WO | 2015164598 A1 | 10/2015 |
| WO | 2015164601 A1 | 10/2015 |
| WO | 2016040962 A1 | 3/2016 |

OTHER PUBLICATIONS

Ali, Mohammad Asif et al. "Syntheses of High-Performance Biopolyamides Derived from Itaconic Acid and Their Environmental Corrosion". Macromolecules, vol. 46, No. 10. XP055298033. May 28, 2013, American Chemical Society, pp. 3719-3725. DOI: 10.1021/ma400395b.
International Search Report PCT/EP2018/069961 dated Oct. 23, 2018 Completed: Oct. 12, 2018 2 pages.
Communication Pursuant to Article 94(3) EPC EP 17182956.7 dated Sep. 6, 2019 5 pages.

* cited by examiner

*Primary Examiner* — Gregory Listvoyb
(74) *Attorney, Agent, or Firm* — Thomas Krivulka

(57) ABSTRACT

A specific polyamide polymer which is obtainable by two specific processes according to the invention. The invention further relates to the use of this polyamide polymer as a functional additive and to detergent compositions, cosmetic compositions, cleaning compositions and adhesive compositions including this polyamide polymer.

7 Claims, No Drawings

WATER-SOLUBLE POLYAMIDE POLYMER AND USE THEREOF AS FUNCTIONAL ADDITIVE

FIELD OF THE INVENTION

The present invention relates to a specific polyamide polymer which is obtainable by two specific processes according to the invention. The invention further relates to the use of this polyamide polymer as a functional additive and to detergent compositions, cosmetic compositions, cleaning compositions and adhesive compositions comprising this polyamide polymer. The present invention also relates to the use of this polyamide in a method for the oxidative lightening and/or dyeing of keratinous fibres, such as hair.

BACKGROUND OF THE INVENTION

Polymers which can be employed as functional additives, e.g., in adhesive compositions, detergent compositions, cosmetic compositions or cleaning compositions are known in the art. Due to the increasing awareness of environmental issues, there exists a need for environmentally friendly, bio-based polymers. The international patent publications WO 2015/164598 A1, WO 2015/164601 A1, WO 2016/040962 A1 and WO 98/22478 A1 disclose such polymers, namely polyimide polymers and pyrrolidinone polymers, respectively.

BRIEF SUMMARY OF THE INVENTION

For certain applications, e.g., adhesive compositions, detergent compositions, cosmetic compositions or cleaning compositions, polymers based on itaconic acid which are water soluble over a broad pH-value range and have a number average molecular weight ($M_n$) of 1.000 to 10.000 g/mol are advantageous. Those polymers—if used as functional additives—have a good stability against other chemicals and different environmental conditions, such as light, heat, exposure to air, especially compared to polymers comprising imide and lactam structures. Therefore, it was an object of the present invention to provide further polymers based on itaconic acid which are comparably environmentally friendly and sufficiently stable, while retaining good water solubility.

For cosmetic applications, it is known to use chelating agents during oxidative hair treatments for dyeing and/or lightening keratinous fibres. In such treatments, the breakdown of melanin pigments and oxidation of hair proteins occurs due to the predominant extremely high alkaline pH value and the presence of oxidizing agents, e.g. hydrogen peroxide or persulfate. But these processes that take place in and on the hair fibre generally involve the risk of attacking and, in the worst case, partially destroying the hair structure. As a result of the processes, customers are uncertain about the reduced mechanical strength of the hair fibres, a roughening of the surface structure, prevented shine and brittleness of the hair.

The water source used by consumers to wash hair contains calcium and magnesium ions, as well as an undesirable amount of redox metal ions. For example, it is already known that a certain amount of copper and iron is present in human hair. The redox metal ions, especially copper or iron, catalyse the redox reaction with hydrogen peroxide under alkaline conditions and lead to the generation of reactive oxygen species (ROS). These ROS are highly active and react very quickly with hair proteins, which can lead to significant hair damage. Complexing agents such as ethylenediaminetetraacetic acid (EDTA), tetrasodium iminodisuccinate (IDS) and ethylenediamine-N,N'-disuccinic acid (EDDS) are therefore used in blonding agents to mask corresponding metal ions. Today, however, there are repeated discussions about the poor biodegradability of common complexing agents. Another disadvantage of EDTA is that EDTA complex Ca and Mg better than transition metal ions such as Cu or Fe. EDTA is not ideal as a special effective complexing agent for Cu or Fe.

The inventors of the present invention have developed two specific processes which result in polyamide polymers according to the present invention. With these processes, pure polyamide polymers can be obtained which do not comprise lactam or pyrrolidinone structures. It has been surprisingly found that, when the polyamide polymers according to the present invention are employed as functional additives in the above-mentioned compositions, they can boost the performance of the respective compositions. For example, they boost the performance of moisture curing adhesives and sealants (especially based on polyurethane or silane-modified polymers), in particular with respect to concrete surface bonding. Further, they improve the washing performance of detergent and cleaning compositions, especially with regard to removing stains. They are also superior in their health and safety characteristics compared to monomeric functional additives, for example standard chelating agents like EDTA, and it is possible to use them in highly compacted laundry detergents.

While not being bound to any theory, it is hypothesized that they positively interact with enzymes and surfactants, for example by having a chelating effect, and thus improve the performance of the detergent, cosmetic or cleaning composition containing the polyamide polymer according to the present invention. Moreover, due to their "homogenous" structure they are more stable to light, heat and oxygen exposure compared to polymers comprising imide and lactam groups.

The processes disclosed herein are furthermore advantageous in that they do not employ a catalyst and are thus more cost efficient. Additionally, one of the methods of synthesis does not employ any solvents and thus provides the polyamide polymer in a more cost-, time- and labour-efficient manner. Consequently, the process that does not use additional solvent according to the present invention is preferred.

In a first aspect, the invention thus relates to a process for the manufacture of a polyamide polymer, wherein itaconic acid or dimethyl itaconate is reacted with di- and/or tri-amine, comprising the steps:
i) providing a di- or triamine, selected from the group encompassing ethylene diamine, compounds of the formula I

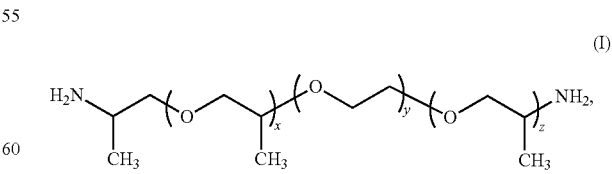

in which x stands for a number in the range of from 0 to 20, y stands for a number in the range of from 0 to 35, and z stands for a number in the range of from 0 to 20, with the proviso that at least one of x, y and z is at least 1, compounds of the formula II

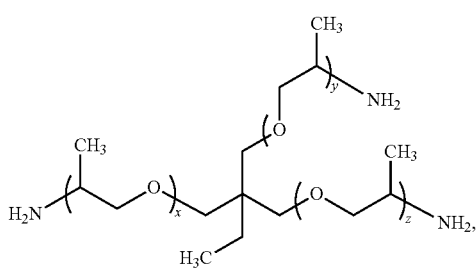

in which x stands for a number in the range of from 0 to 85, y stands for a number in the range of from 0 to 85, and z stands for a number in the range of from 0 to 85, with the proviso that at least one of x, y and z is at least 1 and its mixtures, in a reaction vessel;
ii) adding, preferably under stirring, itaconic acid or dimethyl itaconate in a molar monomer ratio of amine groups to carboxy groups of ii-a) 1:1 to 1:1.9, preferably 1:1 to 1:1.2, more preferably 1:1, or ii-b) 1.9:1 to 1.01:1, preferably 1.2:1 to 1.02:1, to the reaction vessel and heating the obtained mixture.

Preferably the number average molecular weight of the compounds according to formula I does not exceed 2000 g/mol; preferably the number average molecular weight of the compounds according to formula II does not exceed 440 g/mol; and preferably the number average molecular weight of the compounds according to formula III does not exceed 5000 g/mol. Compounds according to formulae I, II, or III are commercially available under the trade name Jeffamine® from Huntsman Corporation. x, y, and z in the ether amine compounds according to formulae I, II, or III may be integers or fractional numbers. Examples for compounds of formula I are those in which x=2.5 and y=z=0 (Jeffamine® D-230), or x=5 and y=z=0 (Jeffamine® D-409), or y=12.5 and x+z=6 (Jeffamine® ED-900). Examples for compounds of formula II and III are those in which x+y+z=5, or x+y+z=6 (Jeffamine® T-403), or x+y+z=85 (Jeffamine® T-5000).

Most preferred are the ethylene diamine and diamine compounds of formula I, and mixtures of diamine compounds of formula I with triamines of formula II and/or formula III; in those mixtures the molar content of diamine compounds of formula I preferably is above 50%.

In various embodiments of said process in step ii) the itaconic acid or dimethyl itaconate is added portion-wise to the reaction vessel, preferably in portions of equal weight, more preferably the individual portions are ½, ⅓, ¼, ⅕, ⅙, ⅐ of the total weight of itaconic acid or dimethyl itaconate to be added.

While in the following the claimed processes are disclosed with reference to itaconic acid or dimethyl itaconate, it is understood that combinations thereof may similarly be employed. Accordingly, in all embodiments disclosed herein, both can be used in combination.

The heating in step ii) may be started with the addition of the itaconic acid or dimethyl itaconate or may be started once the complete amount has been added. In various embodiments of the process, in step ii) the mixture is heated to a temperature between 100° C. and <160° C., preferably to at least 120° C., more preferably to at least 130° C., most preferably to about 140° C., in particular with a rate of 1° C./min, preferably 2.5° C./min, more preferably 3° C./min, most preferably 4° C./min. After the final temperature of step ii) has been reached, the mixture of step ii) may, in a further step iii), be heated to a temperature of 160° C. or more, preferably at least 170° C., more preferably at least 175° C., most preferably to about 185° C. for 3 to 6 hours, preferably for 4 to 5.5 hours, more preferably for 4.5 to 5 hours.

"About", as used herein in relation to a numerical value, means said numerical value±5%. About 140° C. thus relates to a temperature in the range of 133-147° C.

In various embodiments of the processes, after step a-ii) or step a-iii) vacuum is applied, preferably stepwise, to the reaction mixture until a pressure of >800 mbar, preferably 800 to 1 mbar is reached.

In another aspect, the invention relates to a process for the manufacture of a polyamide polymer, wherein itaconic acid or dimethyl itaconate is reacted with the di- or triamine defined above, for example in air or preferably under an inert atmosphere, more preferably under nitrogen, comprising the steps:
a) providing a solution of itaconic acid or dimethyl itaconate in alcohol, preferably methanol, ethanol, propanol or isopropanol, more preferably methanol, in a reaction vessel;
b) adding, preferably dropwise, under stirring a solution of the diamine in the same alcohol as used in step a) to the reaction vessel in a molar monomer ratio of diamine to itaconic acid or dimethyl itaconate of b-a) 1:1 to 1:1.9, preferably 1:1 to 1:1.2, more preferably 1:1, or b-b) 1.9:1 to 1.01:1, preferably 1.2:1 to 1.02:1, preferably over 30 minutes to 3 hours, more preferably for 1 hour to 2 hours, and after the addition is completed, preferably stirring the mixture for 30 minutes to 3 hours, more preferably for 1 hour to 2 hours;
c) removing the alcohol from the mixture, preferably at room temperature for 2 to 30 hours or at a temperature range of 25° C. to 60° C. under vacuum of 40 to 600 mbar, preferably 60 to 150 mbar over 1 to 6 hours, preferably 2 to 4 hours, to obtain a solid precipitate; and preferably heating the precipitate to 40 to 70° C., more preferably 50 to 60° C., under vacuum, preferably stepwise to 600 to 1 mbar, more preferably to 600 to 45 mbar for 30 minutes to 2 hours; and
d) heating the precipitate obtained in step c) to at least 190° C., preferably at least 200° C., more preferably at least 215° C., most preferably about 230° C., preferably with a rate of 1° C./min, preferably 2° C./min, more preferably 3° C./min, and more preferably keeping the precipitate at the final temperature for 30 minutes to 3 hours or 1 hour to 2 hours at a vacuum of 1 to 80 mbar, preferably 20 to 50 mbar.

In still another aspect, the invention also relates to a polyamide polymer obtained or obtainable according to a process of the invention, wherein the polyamide polymer preferably has a weight average molecular weight ($M_w$) of 1,000 to 10,000 g/mol, preferably 2,500 to 5,000 g/mol, as measured via gel permeation chromatography (GPC) using polystyrene standards and a mixture of an aqueous solution of 0.07 M Disodiumhydrogenphosphate (90 vol-%) and acetonitrile (10 vol-%) as elution agent.

In various embodiments, an aqueous solution of 25 wt.-% of the polyamide polymer in water, based on the total weight of the aqueous solution, has a pH-value of 4 to 7, preferably 4 to 5, more preferably 4.3 to 4.6, especially if the molar ratio of amine groups from the di- and/or triamine to carboxy groups from the itaconic acid or dimethyl itaconate in the preparation of the polyamide was below 1:1. Alternatively, in various embodiments, an aqueous solution of 25 wt.-% of the polyamide polymer in water, based on the total weight of the aqueous solution, has a pH-value of 6 to 12, preferably 6 to 8, especially if said molar ratio in the preparation of the polyamide was above 1:1.

It is preferred that the polyamide polymer according to the invention does not contain lactam, pyrrolidinone or polyimide groups. Preparing the polyamide polymer by process for the manufacture according to the invention assures that it will not contain such groups.

In a still further aspect, the invention encompasses the use of the polyamide polymer according to the invention as a functional additive, preferably as enzyme activity booster and/or chelating agent for detergent compositions, cosmetic compositions, adhesive composition and/or cleaning compositions, more preferably for improving the cleaning performance of detergent compositions, cosmetic compositions and cleaning compositions or as an adhesion promoter or filler material in adhesive compositions. Also within the scope of the invention are the respective detergent, cosmetic, cleaning and adhesive compositions that comprise the polymers of the invention.

Detergent compositions comprising the polyamide polymer according to the invention, preferably contain the polymer in an amount of 0.1 to 10 wt.-%, more preferably 0.5 to 5 wt.-%, even more preferred 0.8 to 3 wt.-%, most preferred 1 to 1.5 wt.-%, based on the total weight of the detergent composition.

Cleaning compositions comprising the polyamide polymer according to the invention contain the polymer preferably in an amount of 0.1 to 10 wt.-%, more preferably 1 to 5 wt.-%, even more preferred 1 to 3 wt.-%, most preferred 1 to 1.5 wt.-%, based on the total weight of the cleaning composition.

Adhesive compositions comprising the polyamide polymer according to the invention preferably contain the polymer in an amount of 0.1 to 80 wt.-%, more preferably 5 to 70 wt.-%, even more preferred 10 to 60 wt.-%, most preferred 15 to 50 wt.-%, based on the total weight of the adhesive composition.

Cosmetic compositions comprising the polyamide polymer according to the invention, contain the polymer preferably in an amount of at least 0.00 wt %. Suitably, the polyamide polymer according to the invention is present in an amount ranging from 0.1 to 10 wt.-%, preferably from 0.5 to 10 wt.-%, more preferably 1 to 5 wt.-%, even more preferred 1 to 3 wt.-%, yet more preferred 1 to 2 wt.-%, most preferred 1.4 to 1.8 wt.-% based on the total weight of the cosmetic composition.

Suitably, the cosmetic composition according to the present invention is in the form of a bleaching powder. Thus, according to another aspect of the invention, there is provided a bleaching powder comprising the polyamide polymer according to the invention and typically at least one oxidising agent.

Suitably, the cosmetic composition according to the present invention is in the form of a bleaching paste. Typically, such a cosmetic composition further comprises at least one oxidising agent. Thus, according to another aspect of the invention, there is provided a bleaching paste comprising the polyamide polymer according to the invention and typically at least one oxidising agent.

Methods for the oxidative lightening and/or dyeing of keratinous fibers are also provided herein. Such methods involve the use of the polyamide polymer according to the invention, suitably as an additive in a bleaching powder or as an additive in a bleaching paste.

There is also provided by the present invention a multi-component packaging unit (kit-of-parts) for lightening keratin fibres, in particular human hair, containing at least two components packaged separately from one another. Typically, one of the components of the kit-of-parts is one of the bleaching powders disclosed herein or one of the bleaching pastes disclosed herein.

There is further provided by the present invention, a multi-component packaging unit (kit-of-parts) for changing the colour of keratin fibres, in particular human hair, containing at least three components packaged separately from one another. Typically, one of the components of the kit-of-parts is one of the bleaching powders disclosed herein or one of the bleaching pastes disclosed herein.

DETAILED DESCRIPTION OF THE INVENTION

Disclosed herein are two processes for the manufacture of the polyamide polymer. While the first method is a solvent free method, in the second method alcohol is used as a solvent. However, when not explicitly stated otherwise, all more specific embodiments disclosed herein apply to both processes. Therefore, in the following if reference is made to "a (preferred) process of the present invention" the respective embodiments apply to both processes.

While the processes of the present invention are essentially based on the reaction of itaconic acid or dimethyl itaconate with di- and/or triamine, it should be self-evident that traces of other compounds can be present. However, in a preferred process of the invention, less than 1 wt.-%, preferably less than 0.1 wt.-%, more preferably 0.001 wt.-%, most preferably none monomers other than itaconic acid or dimethyl itaconate and di- and/or triamine are present, based on the total weight of the composition. In a further preferred process of the present invention no catalyst is employed.

In a further preferred process, after heating the obtained precipitate or product of steps (ii), (iii) or (d), the precipitate/product is allowed to cool or actively cooled and the final product can preferably be taken out of the reaction vessel starting at a temperature of 130° C. or less, preferably 100° C. or less, more preferably 70° C. or less, most preferably 50° C. or less.

In the steps of the processes of the present invention where vacuum is applied and the pressure is reduced to a specific value, the pressure can be reduced stepwise or continuously. The skilled person in the field knows which approach is most suitable given the circumstances.

In a preferred embodiment according to the invention, the polyamide polymer is acid-terminated and in a 25 wt.-% aqueous solution exhibits a pH-value of 3 to 7, more preferred 3.5 to 5, most preferred 4 to 4.8. In another preferred embodiment according to the invention the polyamide polymer is amine terminated and exhibits as a 25 wt.-% aqueous solution a pH-value of 7.5 to 12, more preferably 8.5 to 11, most preferably 9 to 10.5.

The processes according to the invention lead to water soluble polyamide polymers. In a further preferred embodiment, the polyamide polymer is water soluble. As used herein "water soluble" means that the solubility at 20° C. in pure water of pH 7 is at least 50 g/L, preferably above 100 g/L, most preferably above 300 g/L, and may for example be as high as or even above 500 g/L, 600 g/L, 700 g/L or 750 g/l. Solubility may for example be measured according to the OECD Guidelines for the Testing of Chemicals, Section 1, Test No. 105: Water Solubility; adopted by the Council on 27 Jul. 1995.

In a preferred embodiment, the obtained polymer has a number average molecular weight ($M_n$) of 500 to 4,000 g/mol, preferably 1,000 to 3,000 g/mol, measured as an aqueous solution via GPC and polystyrene standards.

In a further preferred embodiment the obtained polymer has a polydispersity index of 1.5 to 2.5, preferably 1.7 to 2.1, more preferably 1.8 to 2.0, most preferably 1.9.

The compositions of the invention including the polyamide polymers disclosed herein, i.e., the detergent, cosmetic, cleaning or adhesive composition may comprise further components typical for such compositions. Accordingly, the additional components of said compositions are not particularly limited as long as the components do not negatively interact with the polyamide polymer, e.g., undergo a chemical reaction and precipitate, with the exception of adhesive compositions where a reaction with further components may be desired. In a preferred embodiment, all of the foregoing compositions are aqueous compositions. In preferred embodiments the detergent, cosmetic and cleaning compositions further comprise at least one surfactant and/or perfume.

In a preferred embodiment the adhesive composition is a moisture-curing reactive one component (1K) or two component (2K) adhesive, based on polyurethane with isocyanate termination or a sealant based on a silane-modified polymer.

The polyamide polymer according to the invention may be provided in the form of a solid (typically in powder form) or in the form of an aqueous solution. If provided in the form of an aqueous solution, the polyamide polymer according to the invention preferably has a pH as given above. Suitable cosmetic compositions in which the the polyamide polymer according to the invention may be incorporated include compositions for the oxidative lightening and/or dyeing of keratinous fibres (in particular human hair), shampoos, hair conditioners, hair styling products and body cleansers (such as shower gels and liquid soaps). Such cosmetic compositions may also comprise suitable additives and/or additional components as would be found in conventional compositions. The skilled person is able to select the most appropriate additives and/or additional components based on the nature of the cosmetic composition.

The inventors have surprisingly found that the the polyamide polymer according to the invention exhibit beneficial properties when incorporated into hair products for use in the oxidative lightening and/or dyeing of keratinous fibres—both in terms of their use as chelating agents in suitable hair compositions, and also in terms of mechanical properties exhibited by the treated hair. Without wishing to be bound by theory, the inventors of the present invention believe that the condensate reaction products can be used to complex the copper or iron ions in hair. During hair dyeing and bleaching, significantly less reactive oxygen species (ROS) were detected compared to experiments with conventional complexing agents. Thus, the inventors believe that the advantageous chelating properties of the the polyamide polymer could be attributable to high complexation selectivity for Cu and Fe irons. Thus, the polyamide polymer according to the invention may be incorporated into a complexing agent for use according to the present invention, and according to the methods of the present invention.

The cosmetic compositions of the present invention may also comprise suitable additives and/or additional components as would be found in conventional compositions for use in the oxidative lightening and/or dyeing of keratinous fibres. The skilled person is able to select the most appropriate additives and/or additional components based on the nature of the cosmetic composition. For example, the cosmetic compositions for use in the oxidative lightening and/or dyeing of keratinous fibres may further comprise oxidising agents, alkalising agents, surfactants, oils, fatty components (particularly fatty components with a melting point in the range of 23-110° C.) and polymeric thickeners. Examples of suitable cosmetic compositions may be found, for example in US 2017/0340553 A1 (relating to a bleaching paste and associated compositions, and uses thereof) and US 2018/0008524 A1 (relating to a bleaching powder and associated compositions, and uses thereof).

A further surprising finding of the inventors is the ability of the polyamide polymer according to the invention to be included in conventional bleaching products (for example pastes and powders) without the need for additional substances, and this forms another aspect of the present invention. For example, the present invention provides cosmetic compositions comprising the polyamide polymer according to the invention, wherein no additional additives are present. Such additives include acids, for example succinic acid (or salts thereof), lysine and arginine. Suitably, the cosmetic product of the present invention may consist of solely polyamide polymer according to the invention either as a solid or in an aqueous solution. The polyamide polymer according to the invention may also be dissolved in an organic solvent or in a solvent mixture.

Bleaching powders incorporating the polyamide polymer according to the invention are disclosed herein. The terms "powder" or "powder-like" are to be understood, in accordance with the invention, to mean an administration form formed of individual particles which, at 20° C., is solid and can be poured, the individual particles having particle sizes in the range of from 0.1 μm to at most 1.6 mm. The particle sizes can be determined preferably by means of laser diffraction measurement in accordance with ISO 13320-1 (2009). As appropriate, the grain size of the particles can be adapted to the requirements of the bleaching powder by physical treatment, such as sieving, pressing, granulation or palletisation, or by the addition of specific auxiliaries, so as to enable for example an improved miscibility of the individual powder constituents or the miscibility of the bleaching powder with a hydrogen peroxide preparation. Bleaching powders that are preferred in accordance with the invention have a bulk density in the range of from 500 to 1000 g/l (grams/litre), preferably 550 to 900 g/l, particularly preferably 600 to 820 g/l. The bulk density is determined preferably in accordance with EN ISO 60 (version 01/2000) or DIN ISO 697 (version 01/1984). Unless specified otherwise, all specified temperatures relate to a pressure of 1013 mbar.

A further subject of the present invention is a method for lightening keratin fibres, in particular human hair, in which a bleaching powder according to the invention or a bleaching powder that is preferred in accordance with the invention as disclosed herein is mixed with an oxidation composition which, in each case in relation to its weight, contains 50% by weight to 96% by weight, preferably 70% by weight to 93% by weight, particularly preferably 80% by weight to 90% by weight of water and 0.5% by weight to 20% by weight of hydrogen peroxide and also contains at least one pH adjuster in such an amount that the oxidation composition has a pH value in the range of 2.5 to 5.5, measured at 20° C., is applied directly thereafter to the keratin-containing fibres, is left on the fibres for 5 to 60 minutes, and then the fibres are rinsed with water and the mixture is optionally washed out using a surfactant-containing cleansing agent, wherein the bleaching powder (B) and the oxidation composition (Ox) are preferably mixed with one another in a weight-based ratio (B):(Ox) of 0.2 to 1, particularly preferably 0.3 to 0.8, more preferably 0.4 to 0.7, extremely preferably 0.5 to 0.6.

The oxidation composition used in the lightening method according to the invention contains fundamentally water and hydrogen peroxide. The concentration of hydrogen peroxide is determined on the one hand by the legal requirements and on the other hand by the desired effect. It is 0.5% by weight to 20% by weight, preferably 3% by weight to 12% by weight, particularly preferably 6% by weight to 9% by weight of hydrogen peroxide (calculated as 100% $H_2O_2$), in each case in relation to the weight of the oxidation composition.

The present invention also provides a multi-component packaging unit (kit-of-parts) for changing the colour of keratin fibres, in particular human hair, containing at least two or three components packaged separately from one another, wherein the bleaching powder of the present invention is present in one of the parts.

A multi-component packaging unit comprises a plurality of individual components which are packaged separately from one another, and also a common packaging for these components, for example a collapsible box. The components are provided therein, each separated into different containers. Within the scope of the present invention, a container is understood to mean a wrapping which is present in the form of an optionally re-closable bottle, a tube, a can, a bag, a sachet or a similar wrapping. In accordance with the invention, the wrapping material is not subject to any limitations. However, the wrappings are preferably made of glass or plastic. In addition, the packaging unit can comprise application aids, such as combs, hairbrushes or paintbrushes, personal protective clothing, in particular disposable gloves, and a set of instructions.

In a further preferred embodiment of the invention a bleaching powder according to the invention or a bleaching powder that is preferred in accordance with the invention can be combined with an alkalising composition and with an oxidation composition, which suitably forms a lightening or dyeing agent for keratin fibres. The bleaching powder may be packaged together with the oxidising agent. Alternatively, the bleaching powder may be packaged together with the alkalising agent. A further alternative is that the bleaching powder is packaged separately from both the oxidising agent and the from the alkalising agent. The skilled person is able to select suitable alkalising and oxidation compositions.

Since, when treating keratin fibres, in particular hair, with oxidising agents, in particular with hydrogen peroxide, the dye melanin, which occurs naturally in the fibres, is destroyed to a certain extent, the fibres/hair are/is inevitably lightened, i.e. the colour thereof changes even without the presence of a dye. The term "colour change" in the sense of the present application therefore includes both the lightening and dyeing.

A further subject of the present invention is a method for changing the colour of keratin fibres, in particular human hair, in which a bleaching powder according to the invention or a bleaching powder that is preferred in accordance with the invention as disclosed herein is mixed with an oxidation composition which contains, in each case in relation to its weight, 50% by weight to 96% by weight, preferably 70% by weight to 93% by weight, particularly preferably 80% by weight to 90% by weight of water and 0.5% by weight to 20% by weight of hydrogen peroxide and also contains at least one pH adjuster in such an amount that the oxidation composition has a pH value in the range of 2.5 to 5.5, measured at 20° C., and additionally is mixed with an alkalising composition which contains water and at least one alkalising agent which is selected from ammonia, alkanolamines and mixtures hereof, and has a pH value in the range of 8 to 12, preferably 9 to 11, particularly preferably of 9.5 to 10.5, in each case measured at 20° C., is applied to the keratin-containing fibres directly thereafter, is left on the fibres for 5 to 60 minutes, and the fibres are then rinsed with water and the mixture is optionally washed out using a surfactant-containing cleansing agent, wherein the bleaching powder (B), the oxidation composition (Ox), and the alkalising composition (Alk) are preferably mixed with one another in a weight-based ratio (B):(Ox):(Alk) of (0.7 to 1.3):(2 to 3):(2 to 3), particularly preferably (0.8 to 1.2):(2.3 to 2.7):(2.3 to 2.7), extremely preferably 1:2:2.

The bleaching powders according to the invention and/or the bleaching powders that are preferred in accordance with the invention and/or the alkalising compositions used with preference in accordance with the invention can also contain at least one substantive dye. These are dyes which are drawn directly onto the hair and do not require an oxidising process to form the colour. To dull undesirable residual colour impressions caused by melanin degradation products, in particular in the red or blue spectrum, certain substantive dyes of the complementary colours are particularly preferably contained. Substantive dyes are usually nitrophenylenediamines, nitroaminophenols, azo dyes, anthraquinones or indophenols. Substantive dyes can be anionic, cationic or non-ionic. The substantive dyes are each used preferably in an amount of 0.001% by weight to 2% by weight, in relation to the weight of the bleaching powder or the alkalising composition.

A further subject of the present invention is the use of a bleaching powder as disclosed herein for reducing damage to keratin fibres, in particular human hair, caused by the treatment of these fibres with a mixture of the bleaching powder and an oxidation composition, which, in each case in relation to its weight, contains 50% by weight to 96% by weight, preferably 70% by weight to 93% by weight, particularly preferably 80% by weight to 90% by weight of water and 0.5% by weight to 20% by weight of hydrogen peroxide and has a pH value in the range of 2.5 to 5.5, measured at 20° C.

Bleaching pastes incorporating the polyamide polymer according to the invention are disclosed herein. The terms "paste" or "paste-like" are to be understood, in accordance with the invention, to mean an administration form which, at 20° C., has a viscosity in the range of 200,000 mPas to 1,600,000 mPas, preferably 250,000 mPas to 1,400,00 mPas, particularly preferably 300,000 mPas to 1,000,000 mPas, exceptionally preferably 400,000 mPas to 750,000 mPas. The paste viscosity is preferably determined by means of Brookfield apparatus RVDV II+; spindle no. 96, 4 revolutions per minute, at 20° C.

A further subject of the present invention is a method for lightening keratinic fibres, in particular human hair, in which a bleaching paste according to the invention or a bleaching paste that is preferred in accordance with the invention as disclosed herein is mixed with an oxidation composition (Ox) which, in each case in relation to its weight, contains 50% by weight to 96% by weight, preferably 70% by weight to 93% by weight, particularly preferably 80% by weight to 90% by weight of water and 0.5% by weight to 20% by weight of hydrogen peroxide and also contains at least one pH adjuster in such an amount that the oxidation composition has a pH value in the range of 2.5 to 5.5 at 20° C., is applied directly thereafter to the keratin-containing fibres, is left on the fibres for 5 to 60 minutes, and then the fibres are rinsed with water and the bleaching paste is optionally washed out using a surfactant-containing cleansing agent, wherein the bleaching paste (B) and the oxidation composition (Ox) are preferably mixed with one another in a weight-based ratio (B):(Ox) of 0.2 to 1, particularly preferably 0.3 to 0.8, more preferably 0.4 to 0.7, exceptionally preferably 0.5 to 0.6.

The present invention also provides a multi-component packaging unit (kit-of-parts) for changing the colour of keratin fibres, in particular human hair, containing at least two or three components packaged separately from one another, wherein the bleaching paste of the present invention is present in one of the parts.

In a further preferred embodiment of the invention a bleaching paste according to the invention or a bleaching paste that is preferred in accordance with the invention can be combined with an alkalising composition and with an oxidation composition, which suitably forms a lightening or dyeing agent for keratin fibres. The bleaching paste may be packaged together with the oxidising agent. Alternatively, the bleaching paste may be packaged together with the alkalising agent. A further alternative is that the bleaching paste is packaged separately from both the oxidising agent and the from the alkalising agent.

Thus, a further subject of the present invention is a multi-component packaging unit (kit-of-parts) for lightening keratinic fibres which contains at least two components packaged separately from one another and which is characterised in that
i) the first component (I) is a bleaching paste according to the invention or is a bleaching paste that is preferred in accordance with the invention,
ii) the second component (II) is an oxidation composition which contains, in each case in relation to its weight, 50-96% by weight, preferably 70-93% by weight, particularly preferably 80-90% by weight of water and 0.5-20% by weight of hydrogen peroxide and has a pH value in the range of 2.5 to 5.5, measured at 20° C.,
wherein components (I) and (II) are preferably present in a weight-based ratio to one another (I):(II) of 0.2 to 1, particularly preferably 0.3 to 0.8, more preferably 0.4 to 0.7, exceptionally preferably 0.5-0.6.

A further subject of the present invention is a multi-component packaging unit (kit-of-parts) for changing the colour of keratinic fibres, in particular human hair, containing at least three components packaged separately from one another, wherein
i) the first component (I) is a bleaching paste according to the invention or is a bleaching paste that is preferred in accordance with the invention,
ii) the second component (II) is an oxidation composition which contains, in each case in relation to its weight, 50-96% by weight, preferably 70-93% by weight, particularly preferably 80-90% by weight of water and 0.5-20% by weight of hydrogen peroxide and has a pH value in the range of 2.5 to 5.5, measured at 20° C.,
iii) the third component (III) is an alkalising composition which contains water and at least one alkalising agent, which is selected from ammonia, alkanolamines and mixtures hereof and has a pH value in the range of 8-12, preferably of 9-11, particularly preferably of 9.5-10.5, in each case measured at 20° C.,
wherein the bleaching paste (B), the oxidation composition (Ox) and the alkalising composition (Alk) are preferably present in a weight-based ratio to one another (B):(Ox):(Alk) of (0.7 to 1.3):(2 to 3):(2 to 3), particularly preferably (0.8 to 1.2):(2.3 to 2.7):(2.3 to 2.7).

A further subject of the present invention is a multi-component packaging unit (kit-of-parts) for changing the colour of keratinic fibres, in particular human hair, containing at least three components packaged separately from one another, wherein
i) the first component (I) is a bleaching paste according to the invention or is a bleaching paste that is preferred in accordance with the invention,
ii) the second component (II) is an oxidation composition which contains, in each case in relation to its weight, 50-96% by weight, preferably 70-93% by weight, particularly preferably 80-90% by weight of water and 0.5-20% by weight of hydrogen peroxide and has a pH value in the range of 2.5 to 5.5, measured at 20° C.,
iii) the third component (III) is an alkalising composition which contains water and at least one alkalising agent, which is selected from ammonia, alkanolamines and mixtures hereof and has a pH value in the range of 8-12, preferably of 9-11, particularly preferably of 9.5-10.5, in each case measured at 20° C.,
wherein the bleaching paste (B), the oxidation composition (Ox) and the alkalising composition (Alk) are preferably present in a weight-based ratio to one another (B):(Ox):(Alk) of (0.7-1.3):(2-3):(2-3), particularly preferably (0.8-1.2):(2.3:2.7):(2.3-2.7), exceptionally preferably 1:2:2.

In a further preferred embodiment of the invention a bleaching paste according to the invention or a bleaching paste that is preferred in accordance with the invention can be combined with an alkalising composition and with an oxidation composition to form a lightening or dyeing agent for keratinic fibres.

A further subject of the present invention is a method for changing the colour of keratinic fibres, in particular human hair, in which a bleaching paste according to the invention or a bleaching paste that is preferred in accordance with the invention as disclosed herein is mixed with an oxidation composition which contains, in each case in relation to its weight, 50% by weight to 96% by weight, preferably 70% by weight to 93% by weight, particularly preferably 80% by weight to 90% by weight of water and 0.5% by weight to 20% by weight of hydrogen peroxide and also contains at least one pH adjuster in such an amount that the oxidation composition has a pH value in the range of 2.5 to 5.5, measured at 20° C., and additionally is mixed with an alkalising composition which contains water and at least one alkalising agent which is selected from ammonia, alkanolamines and mixtures hereof and has a pH value in the range of 8 to 12, preferably 9 to 11, particularly preferably of 9.5 to 10.5, in each case measured at 20° C., is applied to the keratin-containing fibres directly thereafter, is left on the fibres for 5 to 60 minutes, and the fibres are then rinsed with water and the bleaching paste is optionally washed out using a surfactant-containing cleansing agent, wherein the bleaching paste (B), the oxidation composition (Ox), and the alkalising composition (Alk) are preferably mixed with one another in a weight-based ratio (B):(Ox):(Alk) of (0.7 to 1.3):(2 to 3):(2 to 3), particularly preferably (0.8 to 1.2):(2.3 to 2.7):(2.3 to 2.7), exceptionally preferably 1:2:2.

The bleaching pastes according to the invention or the bleaching pastes that are preferred in accordance with the invention and/or the alkalising compositions used with preference in accordance with the invention can also contain at least one substantive dye. The dyes suitable for the bleaching paste according to the invention are the same dyes disclosed further above as suitable for the bleaching powders.

As further optional ingredient, the alkalising composition used with preference in accordance with the invention contains at least one oxidation dye precursor, which is preferably selected from one or more developer components and optionally one or more coupler components. The developers and/or coupler components suitable for the bleaching paste according to the invention are the same developers and/or coupler components disclosed further above as suitable for the bleaching powders.

EXAMPLES

A: Analytical Methods
Molecular Weight

Molecular weight analysis was carried out using both Gel Permeation Chromatography (GPC) and Liquid Chromatography Electrospray Ionization Mass Spectrometry (LC-ESI-MS). Aqueous gel permeation chromatography (GPC) was used to determine relative molecular weight averages and molecular weight distribution curves. The product samples were dissolved in distilled water and underwent routine filtration. The elution solvent was an aqueous solution of disodium hydrogen phosphate and chromatographed with an RI (Refractive Index) detector at 30° C. The calibration standard for the analysis was polyethylene glycol. For LC-ESI-MS (Liquid Chromatography Electrospray Ionization Mass Spectrometry), a sample was dissolved in water/acetonitrile. The scanning range was set from 100 to 1250 Da. As is well understood by the skilled person, the GPC measurement is a relative technique and calibration against the standard is required. Further, as the molecular weight values obtained are not absolute, the skilled person understands that the values determined may require conversion in order to characterise absolute values for weight average molecular weight (Mw) and number average molecular weight (Mn). This conversion is well within the ability of the skilled person. Additional molecular weight analysis (such as LC-ESI-MS) can support this conversion. For example, in the characterisation of the products of the present invention where the starting materials were itaconic acid and ethylene diamine (in a ratio of 2:1 w/w), relative Mw values in the range of 1,000 to 1,100 were identified, and Mn values in the range of 950 to 1,050 were identified.

The polydispersity is a ratio (Mw/Mn, as is well understood by the skilled person) so can be used to provide an absolute value of a feature of a product using the relative technique of GPC. For example, in the present case, the inventors identified a polydispersity index ranging from about 1.01 to about 1.04 for the hydrolysed and non-hydrolysed products when the starting materials were itaconic acid and ethylene diamine (in a ratio of 2:1 w/w). This relatively low polydispersity value indicates that the reaction product of the present invention is not a typical mixture of polymers (which would usually exhibit a higher polydispersity index (for example of at least 1.5; typically at least 1.7).

LC-ESI-MS analysis is a technique that characterises the distribution of absolute molecular weight values. The distribution of peaks in the LC-ESI-MS chromatogram supports the relatively low polydispersity index. The analysis of the products of the present invention where the starting materials were itaconic acid and ethylene diamine (in a ratio of 2:1 w/w) identified a distribution of peaks with the main peaks in the LC-ESI-MS chromatogram in the region from about 150 m/z to about 600 m/z. By "main peaks" in the context of the present invention is meant the 3 to 5 peaks exhibiting the highest relative abundance. The products of the present invention may thus be characterised as exhibiting at least two out of the three peaks in the LC-ESI-MS chromatogram with the highest relative abundance less than 500 g/mol. LC-ESI-MS also showed a relatively small number of peaks above 500 g/mol, and particularly few above 650 g/mol. For the peaks in the LC-ESI-MS chromatogram at these higher g/mol values, the relative abundance was very low, i.e. less than 10%. Thus, the reaction products of the present invention may be characterised as exhibiting no peaks in the LC-ESI-MS chromatogram above 650 g/mol with relative abundance of at least 10%.

By comparison with LC-ESI-MS values for absolute molecular weight values, the inventors applied a conversion of ⅓ to the relative molecular weight values identified in the GPC (i.e. the scaling down of the GPC values by ⅓).

FTIR

A sample of the products (in solid, powder form) was used directly for the FTIR measurement. The measurement was conducted with a Spectrum 100 FTIR from the company Perkin Elmer. Measurements were conducted on the UATR-unit with 8 scans; resolution 4 $cm^{-1}$.

B: Synthesis of Polymers

Example 1: Polymer Synthesis According to the Invention, Itaconic Acid/Ethylene Diamine, Molar Ratio 1.01:1, no Solvent In a 2 liter, 5 neck-flask equipped with a nitrogen inlet, thermocouple, overhead stirrer, reflux condenser and load neck, were charged 195 g of ethylene diamine. Subsequently, 426.7 g of itaconic acid were added in portions of 106.7 g every 5 minutes (1.01:1 molar ratio). During the addition of the itaconic acid was observed a considerable increase in temperature (from room temperature to 160° C.) and the suspension like mixture turned into a viscous paste. After the addition of the last portion, due to the high temperature the polycondensation started and there was the formation of water inside the flask (foam creation and the temperature reduction was observed). To promote the reaction of polycondensation the mixture was heated to 175° C. under nitrogen flow and the reflux condenser was replaced by a distillation column. Starting from reaching the set temperature of 175° C. the reaction occurred for about 2 h to achieve total conversion. Afterwards, the final product was discharged from the flask. The final obtained polyamide polymer is brittle yellowish, and hygroscopic. The polyamide structure was confirmed via FT-IR spectroscopy showing typical vibration modes at 1651 $cm^{-1}$ (Amide I) and 1539 $cm^{-1}$ (Amide II) as well as the absence of any imide or lactam modes. Proton NMR (in DMSO) confirmed the obtained structure due to an amide peak around 8.05 ppm and the absence of any double bond peaks around 5 to 7.5 ppm. The polyamide polymer was analysed via GPC in water and showed $M_w$=3900 g/mol, $M_n$=2402 g/mol and a polydispersity of 1.6.

By dissolving the obtained polymer in water (25 wt.-% solution) a pH value of 4.5 was obtained indicating acid terminated polymers without any remaining primary amine groups.

Example 2: Polymer Synthesis According to the Invention, Itaconic Acid/Polyether Amine (Jeffamine® D-230), Molar Ratio 1:1, no Solvent In a 250 mL, 4 neck-flask equipped with a nitrogen inlet, thermocouple, overheadstirrer and reflux condenser, were charged 57.5 g of Jeffamine® D-230. Subsequently, 32.5 g of itaconic acid were added in two equal portions (1:1 molar ratio) within 30 minutes. During the addition of the first itaconic acid portion a slight increase in temperature (from room temperature to 50-60° C.) was observed and after the addition of the second itaconic acid portion the now suspension like mixture showed a further exo-thermic temperature increase to about 120° C. and slight foam creation was observed. To promote the reaction of polycondensation the mixture was heated to 170° C. under nitrogen flow and the reflux condenser was replaced by a distillation column. Starting from reaching the set temperature of 170° C. the reaction occurred for about 3 h to achieve total conversion. Afterwards, the final product was discharged from the flask. The final obtained polyamide polymer is a yellowish-orange and tacky as well as hygroscopic solid at room temperature. The polyamide structure was confirmed via FT-IR spectroscopy showing typical vibration modes at 1661 cm$^{-1}$ (Amide I) and 1538 cm$^{-1}$ (Amide II) as well as the absence of any imide or lactam modes. Proton NMR (in DMSO) confirmed the obtained structure due to an amide peak around 7.85 ppm and the absence of any double bond peaks around 5 to 7.5 ppm.

By dissolving the obtained polymer in water (25 wt.-% solution) a pH value of 7 was obtained indicating a neutral balance between acid and amine groups.

Example 3: Polymer Synthesis According to the Invention, Itaconic Acid/Polyether Amine (Jeffamine® ED-900), Molar Ratio 1:1, no Solvent In a 250 mL, 4 neck-flask equipped with a nitrogen inlet, thermocouple, overheadstirrer and reflux condenser, were charged 90 g of Jeffamine® ED-900. Subsequently, 13 g of itaconic acid were added. During the addition of itaconic acid only a slight increase in temperature (from room temperature to 30-40° C.) was observed. To promote the reaction of polycondensation the mixture was heated to 180° C. under nitrogen flow and the reflux condenser was replaced by a distillation column. Starting from reaching the set temperature of 180° C. the reaction occurred for about 2 h before pressure was stepwise reduced from 300 to 100 mbar at 180° C. over a period of 1.5 h to achieve total conversion. Afterwards, the final product was discharged from the flask. The final obtained polyamide polymer is a yellowish-orange and tacky as well as hygroscopic solid at room temperature. The polyamide structure was confirmed via FT-IR spectroscopy showing typical vibration modes at 1667 cm$^{-1}$ (Amide I) and 1539 cm$^{-1}$ (Amide II) as well as the absence of any imide or lactam modes. Proton NMR (in DMSO) confirmed the obtained structure due to an amide peak around 7.80 ppm and the absence of any double bond peaks around 5 to 7.5 ppm.

By dissolving the obtained polymer in water (25 wt.-% solution) a pH value of 7 was obtained indicating a neutral balance between acid and amine groups.

Example 4: Polymer Synthesis According to the Invention, Itaconic Acid/Ethylene Diamine, Molar Ratio 1:1, with Methanol (MeOH) as Solvent In a single-neck flask along with a magnetic stirring bar 1.66 g of itaconic acid were dissolved in 20 g of MeOH. Afterwards, 0.8 g ethylene diamine were dissolved in 30 g MeOH and then added dropwise into the solution over a one hour period. After the first amine addition, a white precipitate could be immediately noticed. The reaction mixture was stirred at room temperature for additionally two hours. Then, MeOH was removed by evaporation at room temperature over two days and a solid precipitate was obtained. Afterwards, the solid precipitate was kept at 60° C. under vacuum (stepwise from 300 to 100 mbar) for two hours before it was slowly heated (3° C./min) to 220° C. stepwise under vacuum reduction (600 mbar to 45 mbar). At 220° C. the mixture was kept for 2 hours at 45 mbar. Afterwards, the reaction was cooled to 130° C. and the final product was discharged from the flask. The final polyamide polymer was brittle, yellowish to brownish, and hygroscopic. The polyamide structure was confirmed via FT-IR spectroscopy showing typical vibration modes at 1648 cm$^{-1}$ (Amide I) and 1542 cm$^{-1}$ (Amide II) as well as the absence of any imide or lactam modes. Proton NMR (in DMSO) confirmed the obtained structure due to an amide peak around 8.05 ppm and the absence of any double bond peaks around 5 to 7.5 ppm. By dissolving the obtained polymer in water (25 wt.-% solution) a pH value of 4.5 was obtained indicating acid terminated polymers without any remaining primary amine groups.

Example 5: Polymer Synthesis According to the Invention, Dimethyl Itaconate/Ethylene Diamine, Molar Ratio 1:1, with MeOH as Solvent In a single-neck flask along with a magnetic stirring bar 1.57 g of dimethyl itaconate were dissolved in 20 g of MeOH. Afterwards, 0.6 g ethylene diamine were dissolved in 30 g MeOH and then added dropwise into the solution over a one hour period. After the first amine addition, a white precipitate could be immediately noticed. The reaction mixture was stirred at room temperature for additionally two hours. Then, MeOH was removed by evaporation at 60° C. under vacuum at 100 mbar over four hours and a solid precipitate was obtained. Afterwards, the solid precipitate was slowly heated (3° C./min) to 220° C. stepwise under vacuum reduction (200 mbar to 40 mbar). At 220° C. the mixture was kept for 1 hour at 40 mbar. Afterwards, the reaction was cooled to 130° C. and the final product could be discharged from the flask. The final polyamide polymer was brittle, yellowish to brownish, and hygroscopic. The polyamide structure was confirmed via FT-IR spectroscopy showing typical vibration modes at 1652 cm$^{-1}$ (Amide I) and 1540 cm$^{-1}$ (Amide II) as well as the absence of any imide or lactam modes. Proton NMR (in DMSO) confirmed the obtained structure due to an amide peak around 8.05 ppm and the absence of any double bond peaks around 5 to 7.5 ppm. By dissolving the obtained polymer in water (25 wt.-% solution) a pH value of 10 was obtained indicating amine terminated polymer. Residual primary amine groups were confirmed by proton NMR (DMSO) peaks at 2.6 ppm. Moreover, residual ester bonds could be confirmed by a typical IR vibration around 1738 cm$^{-1}$.

Example 6: Non-Hydrolysed Condensate Reaction Product Synthesis According to the Invention: Itaconic Acid/Ethylene Diamine, Molar Ratio 1.25:1 Itaconic Acid:Ethylene Diamine, no Solvent; no Hydrolysis Ethylene diamine was introduced and itaconic acid was added in portions (very light exothermia). After approximately ⅔ of the acid (by weight) was added, a lump was formed in the flask (a paste-like mass). The substance was then gradually heated to 180° C. (bath temperature, oil bath), residual acid was added and the reaction mixture stirred for two hours—while distilling off water; then cooled to room temperature and removed from the flask.

Product: yellow, crystalline substance, very hygroscopic and highly water-soluble over the entire pH range. The molecular weight analysis indicated a polydispersity of 1.09, and a weight average molecular weight (Mw) of around 505 g/mol. FTIR analysis indicated the presence of amide groups (peaks at 1543 and 1645 cm$^{-1}$) in the compounds contained within the reaction product.

Example 7: Hydrolysed Condensate Reaction Product Synthesis According to the Invention: Itaconic Acid/Ethylene Diamine, Molar Ratio 1.25:1 Itaconic Acid:Ethylene Diamine, no Solvent; Hydrolysis The product from Example 6 was adjusted to pH=10 with solid NaOH in water and hydrolysed. Water was then distilled off and the substance dried overnight at 80° C. in a vacuum. The molecular weight analysis indicated a polydispersity of 1.11, and a weight average molecular weight (Mw) of around 468 g/mol. FTIR analysis indicated the presence of amide groups (peaks at 1571 and 1651 cm$^{-1}$), and the absence of lactam/imide groups (no peaks/shoulders around/greater than 1700 cm$^{-1}$) in the compounds contained within the reaction product.

Example 8: Non-Hydrolysed Condensate Reaction Product Synthesis According to the Invention: Itaconic Acid/Ethylene Diamine, Molar Ratio 1.14:1 Itaconic Acid:Ethylene Diamine, no Solvent; no Hydrolysis Ethylene diamine was introduced and itaconic acid was added in portions (very light exothermia). After approximately ⅔ of acid (by weight) was added, a lump was formed in the flask (a paste-like mass). The substance was then gradually heated to 180° C. (bath temperature, oil bath), residual acid was added and the reaction mixture stirred for two hours—while distilling off water; then cooled to room temperature and removed from the flask.

Product: yellow, crystalline substance, very hygroscopic and highly water-soluble over the entire pH range. The molecular weight analysis indicated a polydispersity of 1.11, and a weight average molecular weight (Mw) of around 550 g/mol. FTIR analysis indicated the presence of amide groups (peaks at 1543 and 1646 cm$^{-1}$) in the compounds contained within the reaction product.

Example 9: Hydrolysed Condensate Reaction Product Synthesis According to the Invention: Itaconic Acid/Ethylene Diamine, Molar Ratio 1.14:1 Itaconic Acid:Ethylene Diamine, no Solvent; Hydrolysis The product from Example 8 was adjusted to pH=10 with solid NaOH in water and hydrolysed. Water was then distilled off and the substance dried overnight at 80° C. in a vacuum. The molecular weight analysis indicated a polydispersity of 1.15, and a weight average molecular weight (Mw) of around 600 g/mol. FTIR analysis indicated the presence of amide groups (peaks at 1554 and 1651 cm$^{-1}$), and the absence of lactam/imide groups (no peaks/shoulders around/greater than 1700 cm$^{-1}$) in the compounds contained within the reaction product.

Comparative Example 10: Polymer Synthesis not According to the Invention, Itaconic Acid/Hexamethylene Diamine, Molar Ratio 1:1

In a 3 neck flaks equipped with a thermocouple, overheadstirrer and distillation arm where charged approximately 91 g of hexamethylene diamine. Subsequently, 100 g of itaconic acid were added in portions of 20 g (1:1 molar ratio). After a couple of minutes the suspension like mixture turned into a viscous paste. In parallel, the reaction mixture was heated over 30 minutes to 140° C. After the addition of the last portion of itaconic acid the reaction mixture was heated to 200° C. and kept at this temperature for about 3 hours. Afterwards the reaction was cooled to 130° C. and the final product could be discharged from the reactor. The final product was a gel-like, yellowish to brownish polyamide polymer. The polyamide structure was confirmed via FT-IR spectroscopy showing typical vibration modes at 1650 cm$^{-1}$ (Amide I) and 154 cm$^{-1}$ (Amide II) as well as the absence of any imide or lactam modes. Proton NMR (in DMSO) confirmed the obtained structure due to an amide peak around 8.05 ppm and the absence of any double bond peaks around 5 to 7.5 ppm. The polyamide polymer is insoluble in water and thus not suitable according to the present invention.

Comparative Examples 11 to 14: Polymer Synthesis not According to the Invention, Itaconic Acid/Hexamethylene Diamine or Ethylene Diamine, Molar Ratio 2:1

Comparative examples 11 to 14 were performed according to examples 1 to 3 and comparative example 10, respectively, with the exception that in both cases itaconic acid was used in excess (molar ratio itaconic acid to ethylene diamine/hexamethylene diamine 2:1). In all the comparative examples, a mixture of imide and lactam structures were obtained as confirmed by the absence of any amide II vibration around 1510 to 1550 cm$^{-1}$ within the IR spectra as well as the presence of imide and lactam modes between 1700 and 1720 cm$^{-1}$. Proton NMR analyses confirmed the presence of imide structures due to proton NMR (DMSO) signals around 5.6, 6.05, 6.48 and 1.9 ppm as well as lactam structures due to signals at 2.4, 3.25 and 12.6. Furthermore, proton NMR didn't show any amide peak at about 8 ppm.

C: Washing Performance Tests

Example 15 and Comparative Example 16

To a commercially available liquid laundry detergent (comparative example 16) was added 1.5 wt.-%, based on the total weight of the total composition of the polyamide polymer obtained according to example 1 (example 15). The liquid laundry detergent contained inter alia acids, anionic and non-ionic surfactants, perfume, colouring agent and enzymes.

The washing test was performed on several stains in a common washing machine (Miele W1514) at 40° C., cotton program, 1200 rpm, tab water, 66 mL of the liquid laundry detergents, respectively, and 3.5 kg of laundry. The whiteness, i.e. the brightening of the sheets containing the stains, was determined photometrically as an indication of wash performance. A Minolta CM508d spectrometer device was used, which was calibrated beforehand using a white standard provided with the unit. In the following the type of stains are listed where a significant improvement could be obtained with the composition according to example 15 in comparison to the composition of comparative example 16.

Salad dressing/natural black (CFT C-S-06)
Equest (Equest cooked beef fat)
WFK (Garden soil, accredited)
Jade lipstick (Sweet Nectarine 83)
Sans Soucis make up (Bronze Rose Nr. 40)

Lòreal make up (le teint perfect match)
Mousse au chocolat cold (Dr. Oetker, mixed with water)
Blood/milk/ink (CFT C-05 and EMPA 117)
Cocoa (CFT C-S-02 and EMPA 112)
Chocolate crème (EMPA 160)
Chocolate pudding (EMPA 165)
Milk/carbon black (H-MR-B)
Oatmeal/Chocolate (CFT-C-S-54)
Blood/Beeffat (CFT-C-S-75)

D: Hair Bleaching Tests

Material

Hair samples: Kerling international European Natural Hair 7/0 (Backnang, Germany)

Hair clamps: plastic tabs, code 900.0320 (Dia-Stron Ltd, UK)/hair clamped with liquid epoxy resin Devices: Universal-Dimensions-Measuring-Device UDM 5000A, (Zimmer GmbH, Darmstadt, Germany)

Stress-Strain-System MTT 680 with control unit UV 1000 (Dia-Stron Ltd, UK)

Software: UvWin 1.32.1000 (Dia-Stron Ltd, UK)

Treatment 50 single hair fibers (length between clamps 3 cm) were used for each product and for the reference. The bleaching was performed twice on single hair fiber under the following conditions: 30 g of bleaching powder were mixed with 60 g developer solution (9% $H_2O_2$). The hair was soaked in the bleaching mixture for 45 min at 32° C. Afterwards the fibers were rinsed with tap water for 120 seconds. Finally, the fibers were blow-dried for 60 minutes. This procedure was repeated once. The treated hair fibers were stored for at least 48 hours.

Cysteic Acid Test

In order to measure hair damage induced by the bleaching treatment, the amount of cysteic acid on each treated hair strand was determined by quantitative NIR spectroscopy. The spectra were recorded with an MPA™ FT-NIR Spectrometer from Bruker Optik GmbH. The infrared range including the wavenumber range from 12,500 $cm^{-1}$ to 4,000 $cm^{-1}$ was used to characterize the overtone and combination vibrations of e.g. CH, OH and NH groups. The measurement was performed at six different positions on each hair strand with the integration sphere module in diffuse reflection. For the analysis of the measured NIR spectra, the wavenumber range from 7,300 $cm^{-1}$ to 4,020 $cm^{-1}$ was chosen. The NIR spectra of cysteine show characteristic absorption bands in the wavenumber range from 6,200 $cm^{-1}$ to 5,500 $cm^{-1}$. If hair is oxidatively damaged (i.e., the level of cysteic acid in the hair increases), the cysteic acid bands at 5020 $cm^{-1}$ to 4020 $cm^{-1}$ in the NIR spectrum will be shown. Three hair strands were treated and measured for each bleaching procedure (each formulation). The average value was calculated from the eighteen measurements for each formulation. The quantitative evaluation of the spectra was carried out by computer.

Colour Difference

To assess the colour loss caused by shampooing, the colour difference ΔE measured on the respective strands was determined. The colour difference, also referred to as dE or ΔE, can readily be determined by colourimetry by employing a colourimeter, via which the colours in the L*,a*,b* colour space were measured, a colourimeter from Datacolour, Type Spectraflash 450 in Firma X-right, Typ exact, for example. The L*,a*,b* colour space means the CIELAB colour space. The L-value denotes the lightness of the colour (black-white axis); the higher the value for L, the lighter the colour. The a-value denotes the red-green axis of the system; the higher this value, the more the colour is shifted into the red. The b-value denotes the yellow-blue axis of the system; the higher this value, the more the colour is shifted into the yellow. The colour shift ΔE, i.e. the colour difference between two (hair) colours, for which a L*,a*,b* value combination was determined in each case, is calculated according to the following formula:

$$\Delta E = (\Delta L^2 + \Delta a^2 + \Delta b^2)^{0.5}$$

The higher the value for ΔE, the more pronounced the colour difference, i.e. the higher the amount of colour washed out and the lower the fastness to washing of the dye.

Example 17: Hair Bleach Test

Each of the polymers prepared in examples 6 or 9 were incorporated in bleaching compositions (a mixture of a Blonde powder and a developer) and various properties thereof tested. The compositions of the present invention were compared with those incorporating conventional complexing agents (EDTA, EDDS and IDS), as well as with a composition comprising a hair damage repair agent.

Developer Formulation:

| Ingredient | wt % |
| --- | --- |
| Aqua (Water, Eau) | 69.0 |
| Paraffinum Liquidum (Mineral Oil) | 17.0 |
| Hydrogen Peroxide | 9.0 |
| Cetearyl Alcohol | 3.5 |
| PEG-40 Castor Oil | 0.7 |
| Sodium Cetearyl Sulfate | 0.3 |
| Etidronic Acid | 0.18 |
| Potassium Hydroxide | 0.1 |
| Disodium Pyrophosphate | 0.09 |
| 2,6-Dicarboxypyridine | 0.09 |
| Sodium Benzoate | 0.03 |
| Sodium Sulfate | 0.01 |

Blonde Powder:

| Ingredient | wt % |
| --- | --- |
| Potassium Persulfate | 31.70 |
| Sodium Silicate | 27.00 |
| Magnesium Carbonate Hydroxide | 12.40 |
| Ammonium Persulfate | 9.90 |
| Aqua (Water, Eau) | 9.00 |
| Paraffinum Liquidum (Mineral Oil) | 4.30 |
| Cellulose Gum | 2.00 |
| Polymer of the invention (Inventive formulations I or II) or comparative agent (Comparative Formulations I, II, III or IV) | 1.60 |
| Acrylates Copolymer | 1.00 |
| Silica | 0.65 |
| Sodium Hexametaphosphate | 0.20 |
| Potassium Sulfate | 0.20 |
| Ammonium Sulfate | 0.05 |

The following formulations were prepared using a 2:1 (w/w) mixture of above developer and the above Blonde powder:

Inventive formulation I: where the complexing agent is the non-hydrolysed product from Example 6

Inventive formulation II: where the complexing agent is the hydrolysed product from Example 9

Comparative formulation I: where the complexing agent is EDTA

Comparative formulation II: where the complexing agent is a combination of EDTA with a hair damage repair agent Comparative formulation III: where the complexing agent is IDS
Comparative formulation IV: where the complexing agent is EDDS The resulting products had the following composition:

| Ingredient | wt % |
|---|---|
| Aqua (Water, Eau) | 49.00 |
| Paraffinum Liquidum (Mineral Oil) | 12.74 |
| Potassium Persulfate | 10.60 |
| Sodium Silicate | 9.00 |
| Hydrogen Peroxide | 6.00 |
| Magnesium Carbonate Hydroxide | 4.13 |
| Ammonium Persulfate | 3.30 |
| Cetearyl Alcohol | 2.33 |
| Cellulose Gum | 0.67 |
| Polymer of the invention (Inventive formulations I or II) or comparative agent (Comparative Formulations I, II, III or IV) | 0.53 |
| PEG-40 Castor Oil | 0.47 |
| Acrylates Copolymer | 0.33 |
| Silica | 0.22 |
| Sodium Cetearyl Sulfate | 0.20 |
| Etidronic Acid | 0.12 |
| Potassium Hydroxide | 0.06 |
| Potassium Sulfate | 0.07 |
| Sodium Hexametaphosphate | 0.06 |
| 2,6-Dicarboxypyridine | 0.06 |
| Disodium Pyrophosphate | 0.06 |
| Sodium Benzoate | 0.02 |
| Ammonium Sulfate | 0.02 |
| Sodium Sulfate | 0.01 |

With reference to the following table, based on the cysteic acid content, the hair strand appeared to be significantly less damaged than the formulation with EDDS or IDS with the application of the inventive formulations. Also with reference the following table, the colour shift of the compositions according to the invention in comparison to the product comprising the hair damage repair agent (using Comparative Formulation 2) could not be detected by untrained eyes (i.e. the colour shift value is less than 2).

Results: Hair Damage Test and Colour Shift Test

| | amount of cysteic acid | Colour shift relative to Comparative Formulation II |
|---|---|---|
| Inventive formulation I | 5.0 | 0.98 |
| Inventive formulation II | 5.3 | 1.23 |
| Comparative Formulation III | 6.6 | 1.73 |
| Comparative Formulation II | 6.8 | — |
| Comparative Formulation I | 7.1 | not determined |
| Comparative Formulation IV | 7.2 | 4.15 |

What is claimed is:

1. A process for the manufacture of a polyamide polymer by reacting itaconic acid or dimethyl itaconate with a di- and/or triamine, comprising the steps:
   i) providing a di- or triamine, selected from the group encompassing ethylene diamine, compounds of the formula I

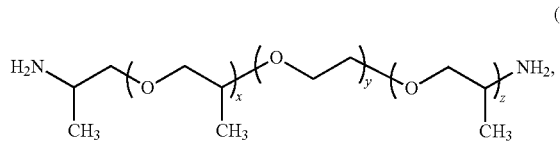

(I)

in which x stands for a number in the range of from 0 to 20, y stands for a number in the range of from 0 to 35, and z stands for a number in the range of from 0 to 20, with the proviso that at least one of x, y and z is at least 1, compounds of the formula II

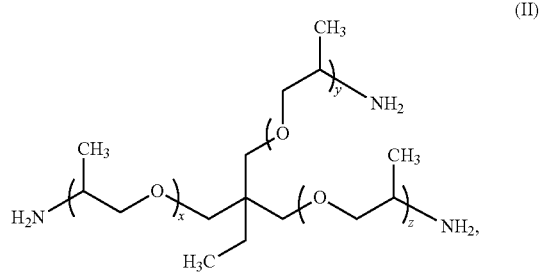

(II)

in which x stands for a number in the range of from 0 to 6, y stands for a number in the range of from 0 to 6, and z stands for a number in the range of from 0 to 6, with the proviso that at least one of x, y and z is at least 1, compounds of the formula III

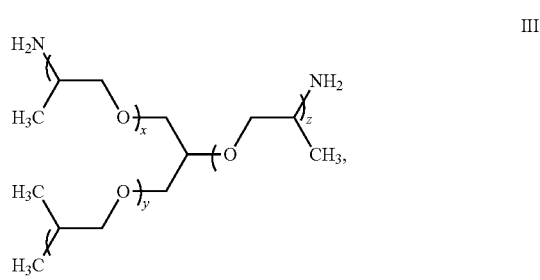

III in which x stands for a number in the range of from 0 to 85, y stands for a number in the range of from 0 to 85, and z stands for a number in the range of from 0 to 85, with the proviso that at least one of x, y and z is at least 1,
and its mixtures, in a reaction vessel;
   ii) adding itaconic acid or dimethyl itaconate in a molar monomer ratio of amine groups to carboxy groups of ii-a) 1:1 to 1:1.9, or ii-b) 1.9:1 to 1.01:1, to the reaction vessel and heating the obtained mixture;
and wherein the process comprises no solvent.

2. The process according to claim 1, wherein in step ii) the itaconic acid or dimethyl itaconate is added portion-wise to the reaction vessel.

3. The process according to claim 1, wherein in step ii) the mixture is heated to a temperature of 100° C. to <160° C.

4. The process according to claim 3, wherein after the final temperature of step ii) has been reached, the mixture of step ii) is in a further step iii) heated to a temperature of 160° C. or more.

5. The process according to claim 3, wherein after step ii) or step iii) vacuum is applied to the reaction mixture until a pressure of 800 mbar or less is reached.

6. The process according to claim 1, wherein itaconic acid or dimethyl itaconate is added under stirring to the reaction vessel.

7. The process according to claim 5, wherein after step ii) or step iii) vacuum is applied to the reaction mixture until a pressure of up to 1 mbar is reached.

* * * * *